US010376229B2

(12) United States Patent
Tamura et al.

(10) Patent No.: US 10,376,229 B2
(45) Date of Patent: Aug. 13, 2019

(54) COMPUTED TOMOGRAPHIC MAMMOGRAPHY SYSTEM

(71) Applicant: CANON KABUSHIKI KAISHA, Tokyo (JP)

(72) Inventors: Miki Tamura, Nagareyama (JP); Takeo Tsukamoto, Kawasaki (JP)

(73) Assignee: Canon Kabushiki Kaisha, Tokyo (JP)

( * ) Notice: Subject to any disclaimer, the term of this patent is extended or adjusted under 35 U.S.C. 154(b) by 120 days.

(21) Appl. No.: 15/022,864

(22) PCT Filed: Sep. 10, 2014

(86) PCT No.: PCT/JP2014/004658
§ 371 (c)(1),
(2) Date: Mar. 17, 2016

(87) PCT Pub. No.: WO2015/040828
PCT Pub. Date: Mar. 26, 2015

(65) Prior Publication Data
US 2016/0228083 A1    Aug. 11, 2016

(30) Foreign Application Priority Data

Sep. 19, 2013  (JP) ................................ 2013-193906

(51) Int. Cl.
*A61B 6/03*   (2006.01)
*A61B 6/00*   (2006.01)
*H01J 35/16*  (2006.01)
*H05G 1/02*   (2006.01)

(52) U.S. Cl.
CPC .............. *A61B 6/502* (2013.01); *A61B 6/032* (2013.01); *H01J 35/16* (2013.01); *H05G 1/02* (2013.01); *H05G 1/025* (2013.01); *H01J 2235/087* (2013.01)

(58) Field of Classification Search
CPC .. A61B 6/00; A61B 6/03; A61B 6/032; A61B 6/502; A61B 6/035; H01J 35/16; H05G 1/02; H05G 1/025
USPC ................................................. 378/4, 15, 37
See application file for complete search history.

(56) References Cited

U.S. PATENT DOCUMENTS

| 6,164,820 | A | 12/2000 | Hell et al. |
| 6,987,831 | B2 | 1/2006 | Ning |
| 2008/0037703 | A1* | 2/2008 | Ting .................... A61B 6/466 378/37 |
| 2008/0317202 | A1 | 12/2008 | Partain et al. |
| 2010/0189223 | A1 | 7/2010 | Eaton et al. |

(Continued)

FOREIGN PATENT DOCUMENTS

| JP | 2007-097610 A | 4/2007 |
| JP | 2011-504647 A | 2/2011 |

(Continued)

*Primary Examiner* — Jurie Yun
(74) *Attorney, Agent, or Firm* — Canon U.S.A., Inc. I.P. Division

(57) ABSTRACT

A computed tomographic mammography system is provided with, as an X-ray tube 1A, a transmission type X-ray tube including a target 2 which includes a target layer 2a that generates X-ray upon irradiation of an electron beam and a supporting substrate 2b through which the X-ray generated upon irradiation of the electron beam to the target layer 2a passes, an electron emission source 3 for emitting an electron beam toward the target layer 2a.

33 Claims, 11 Drawing Sheets

(56) References Cited

U.S. PATENT DOCUMENTS

2011/0133094 A1 6/2011 Seppi et al.
2012/0051496 A1 3/2012 Wang et al.

FOREIGN PATENT DOCUMENTS

| JP | 2013-504365 A | 2/2013 |
| JP | 2013-122906 A | 6/2013 |
| WO | 2012048000 A2 | 4/2012 |

* cited by examiner

[Fig. 1]
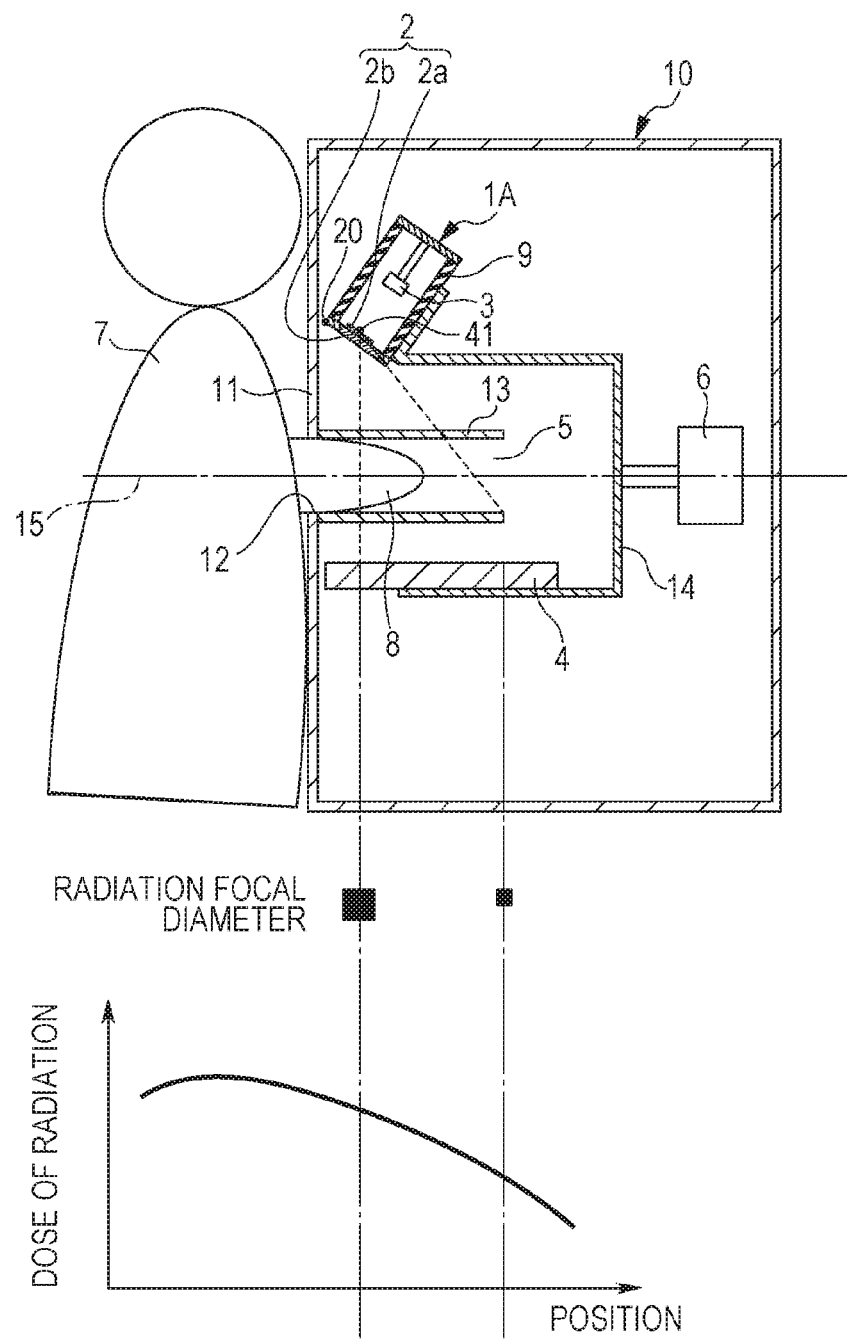

[Fig. 2]
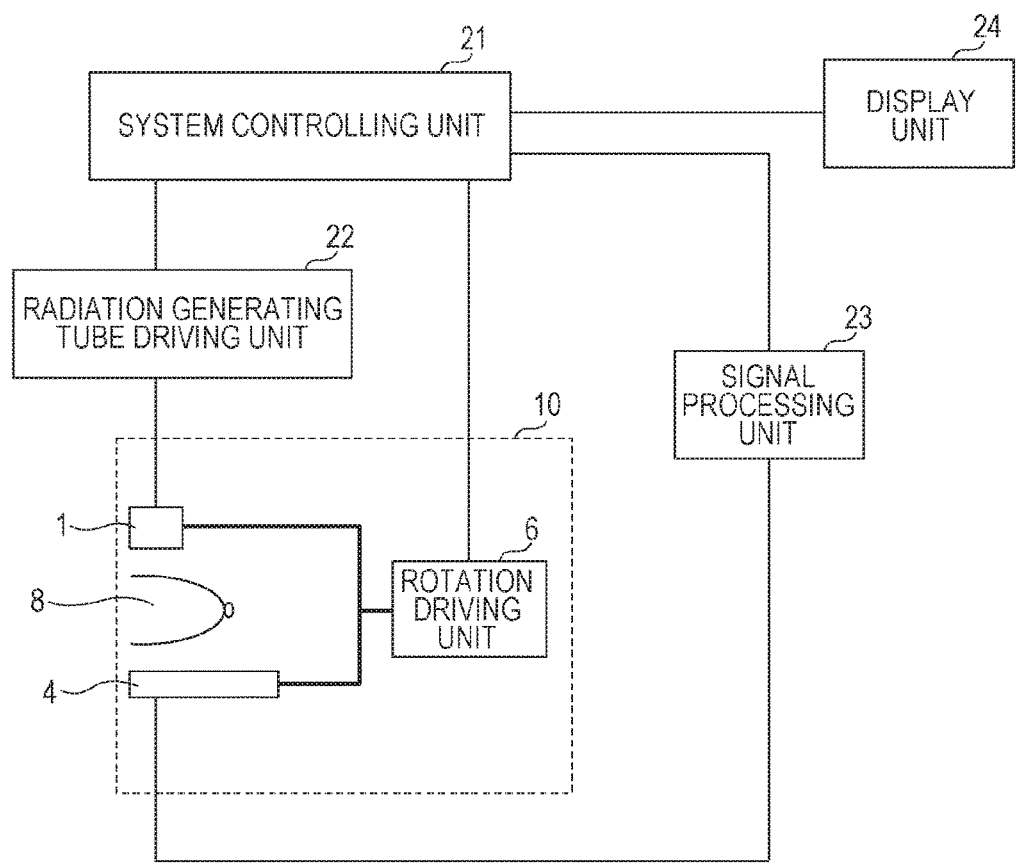

[Fig. 3]
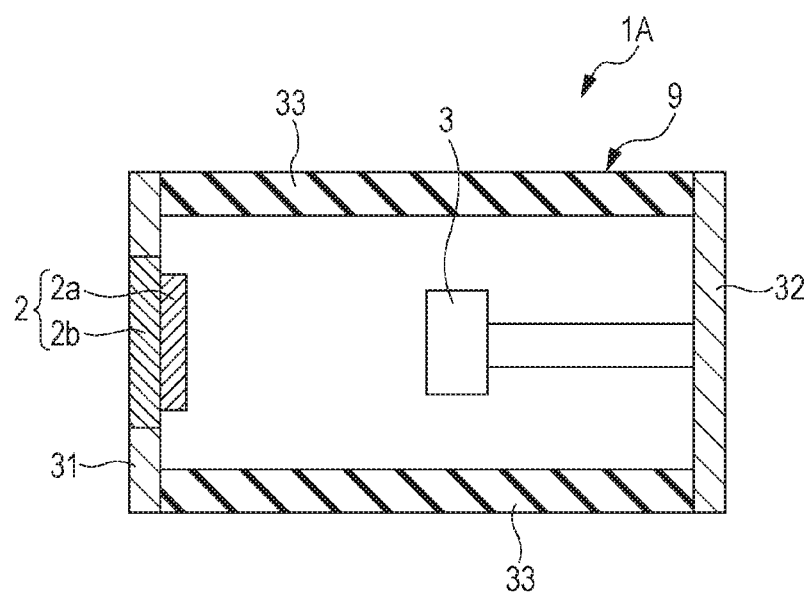

[Fig. 4]
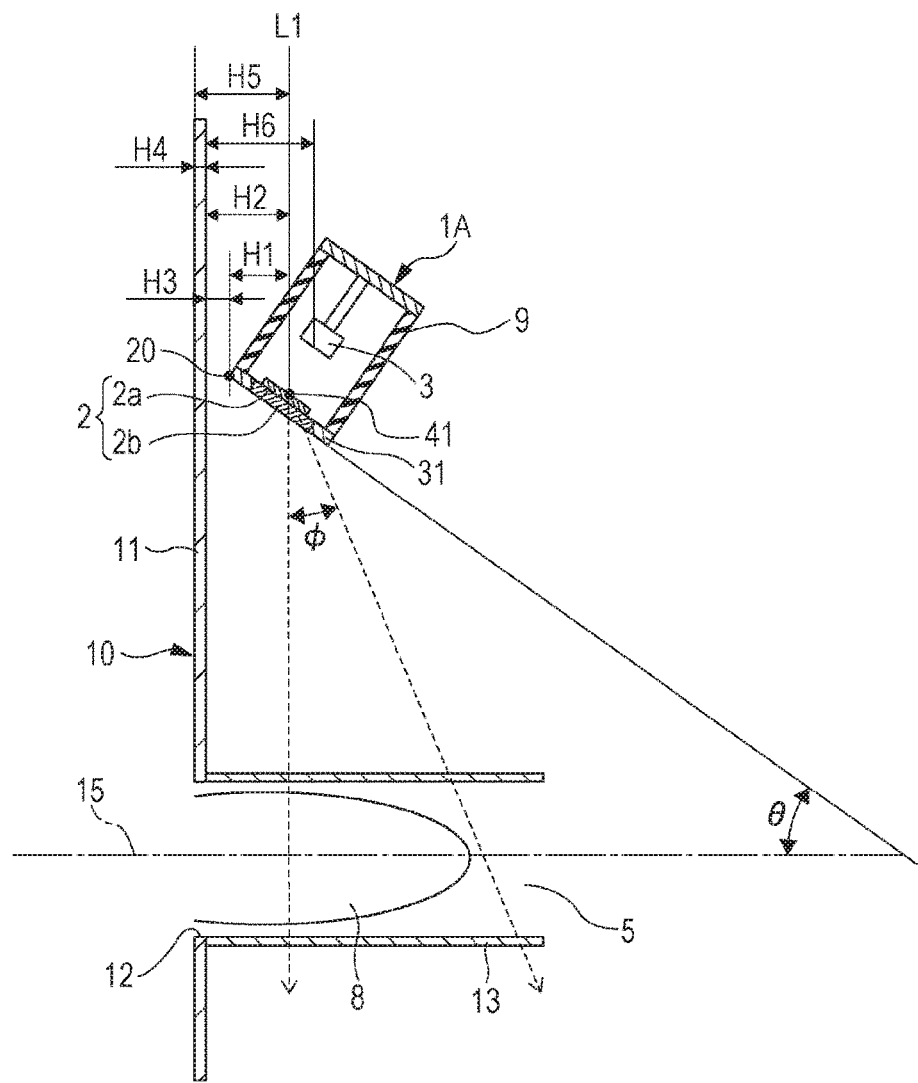

[Fig. 5]
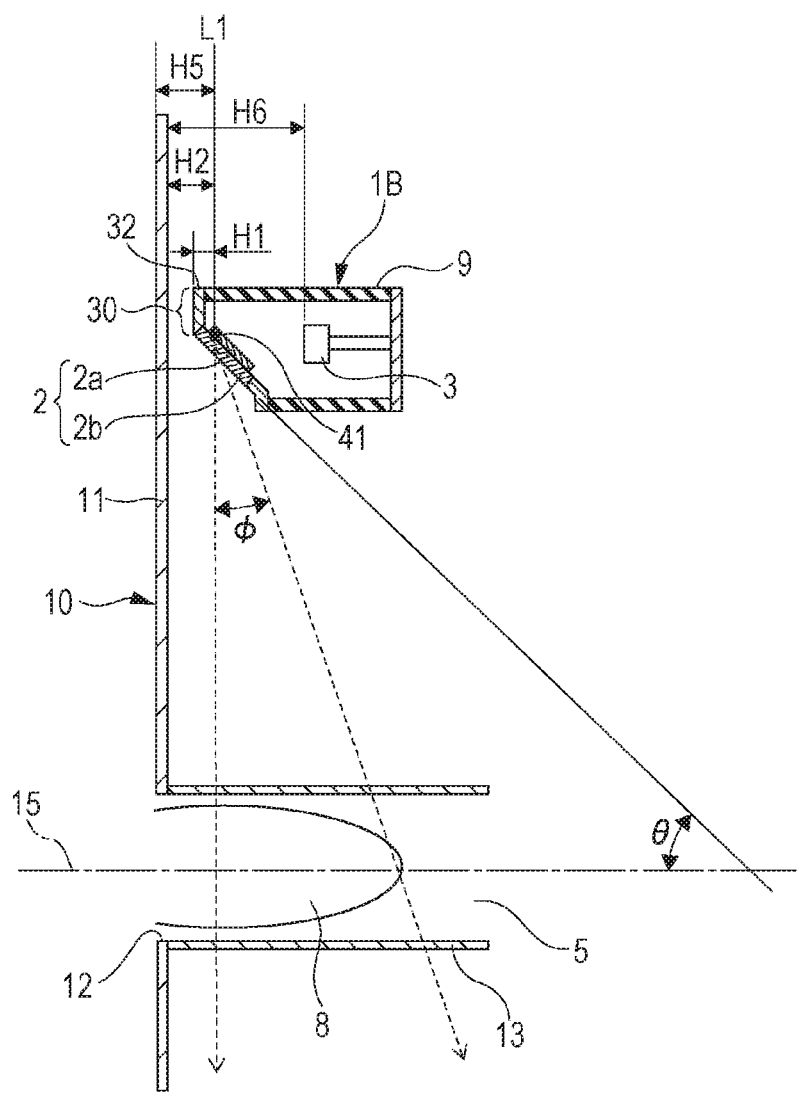

[Fig. 6]
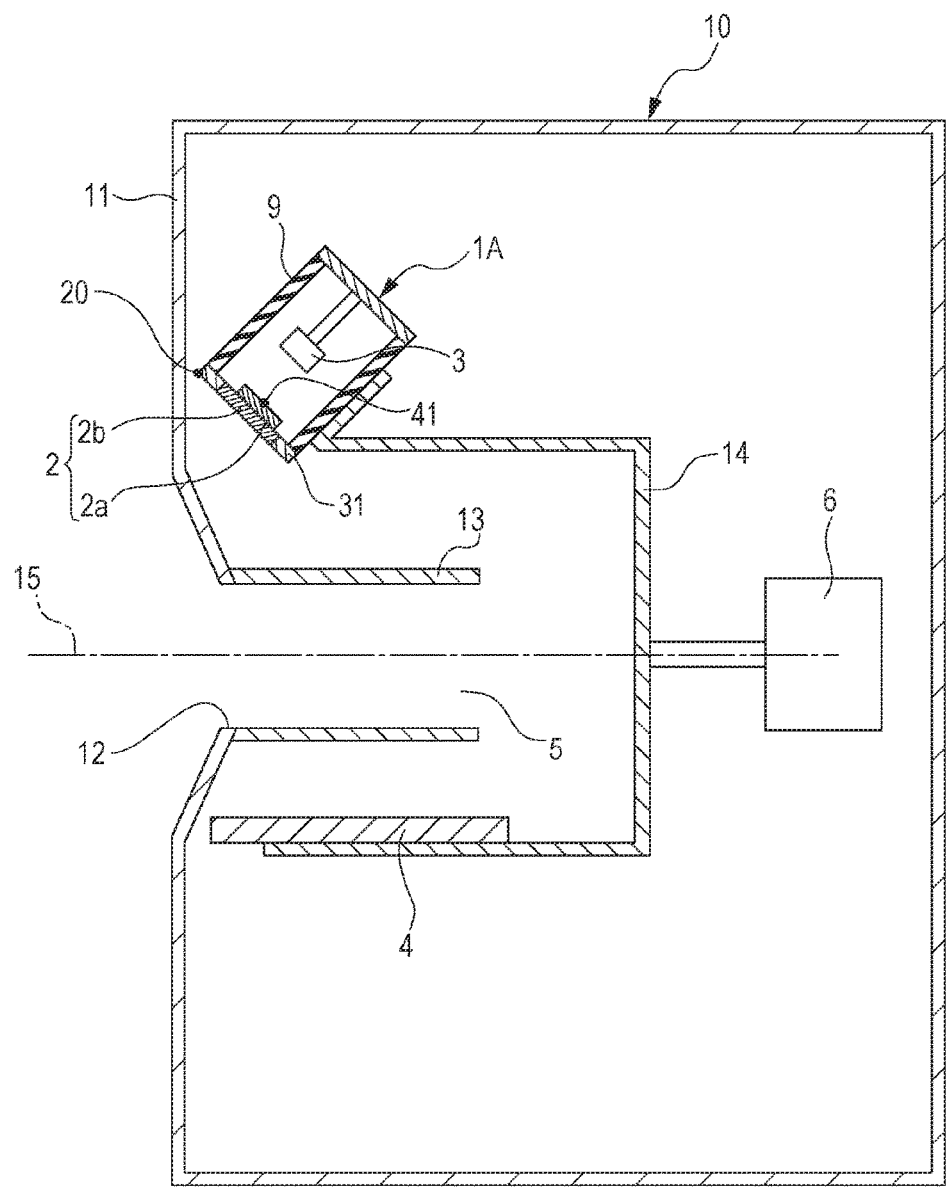

[Fig. 7]
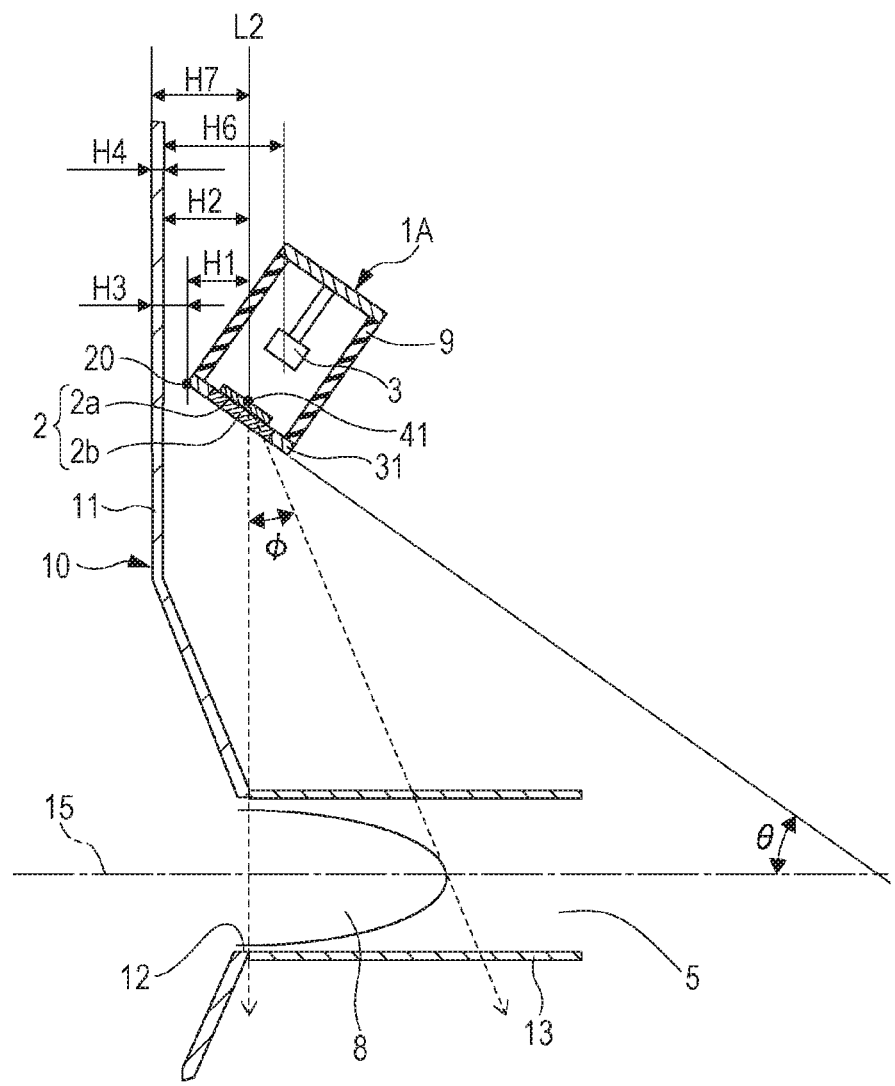

[Fig. 8]
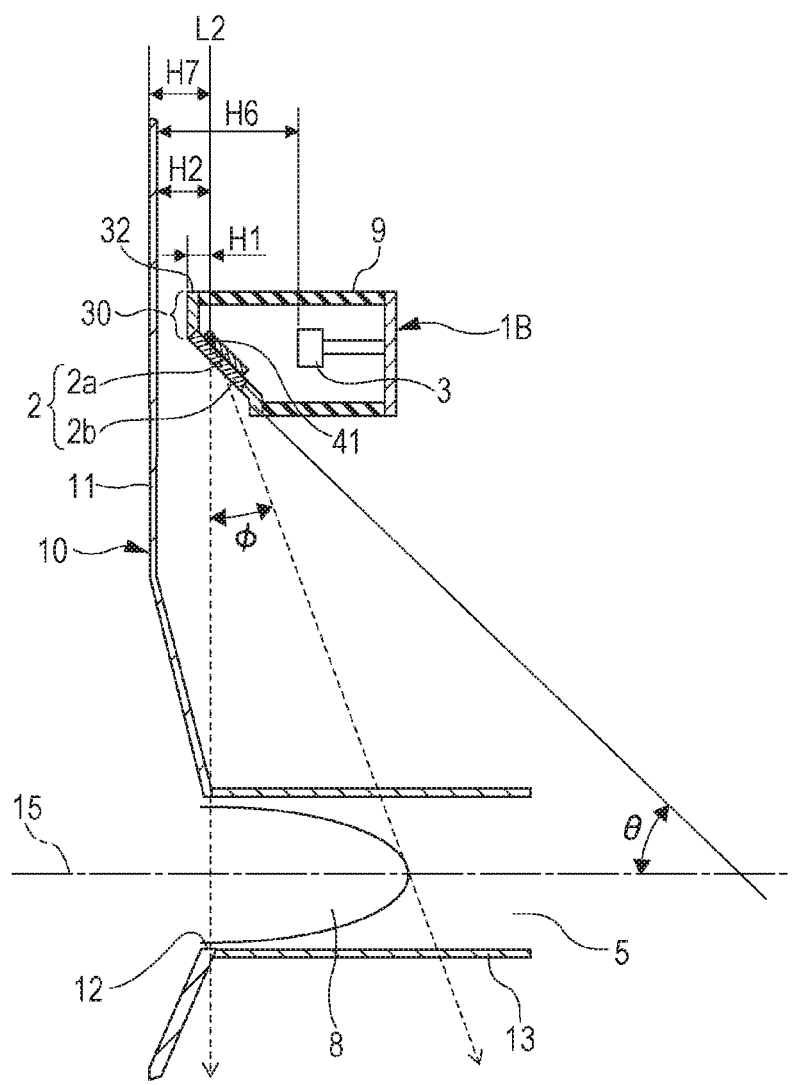

[Fig. 9A]
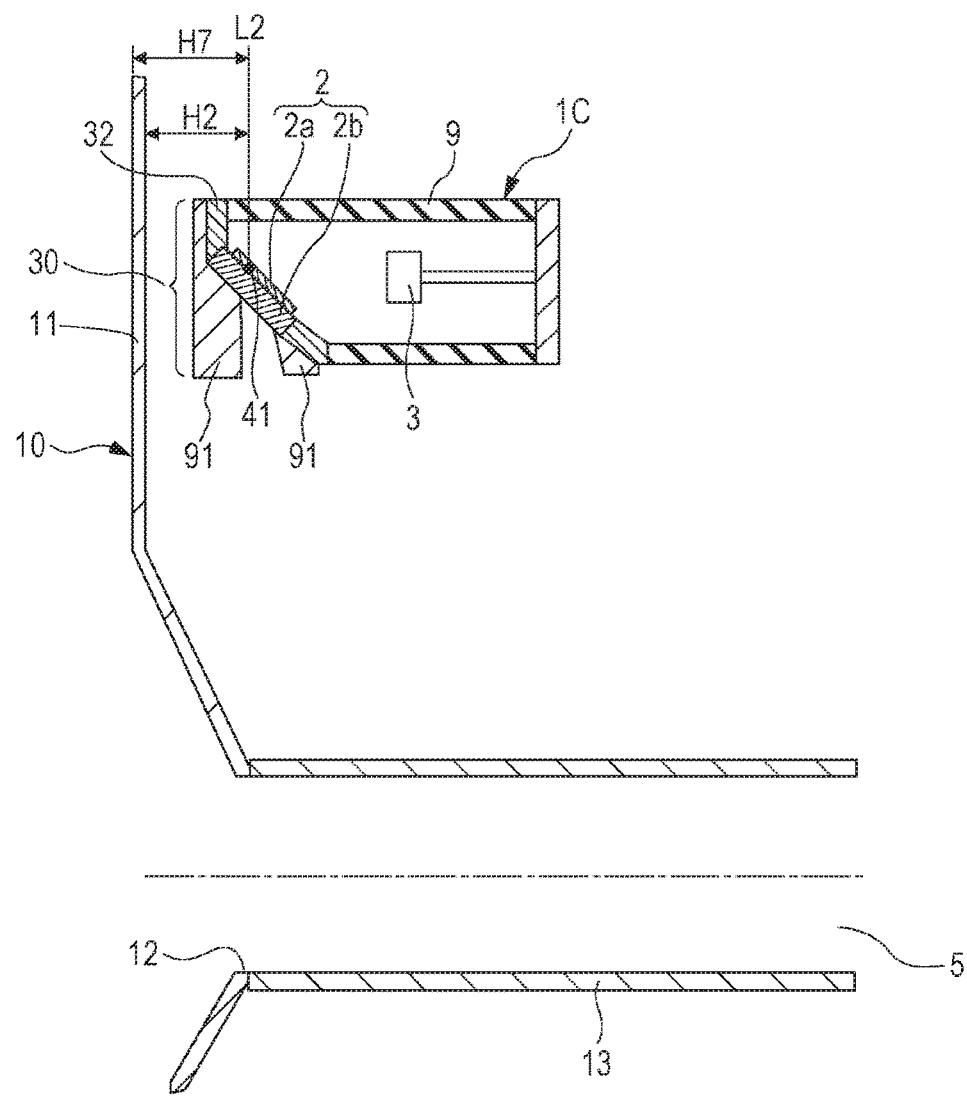

[Fig. 9B]
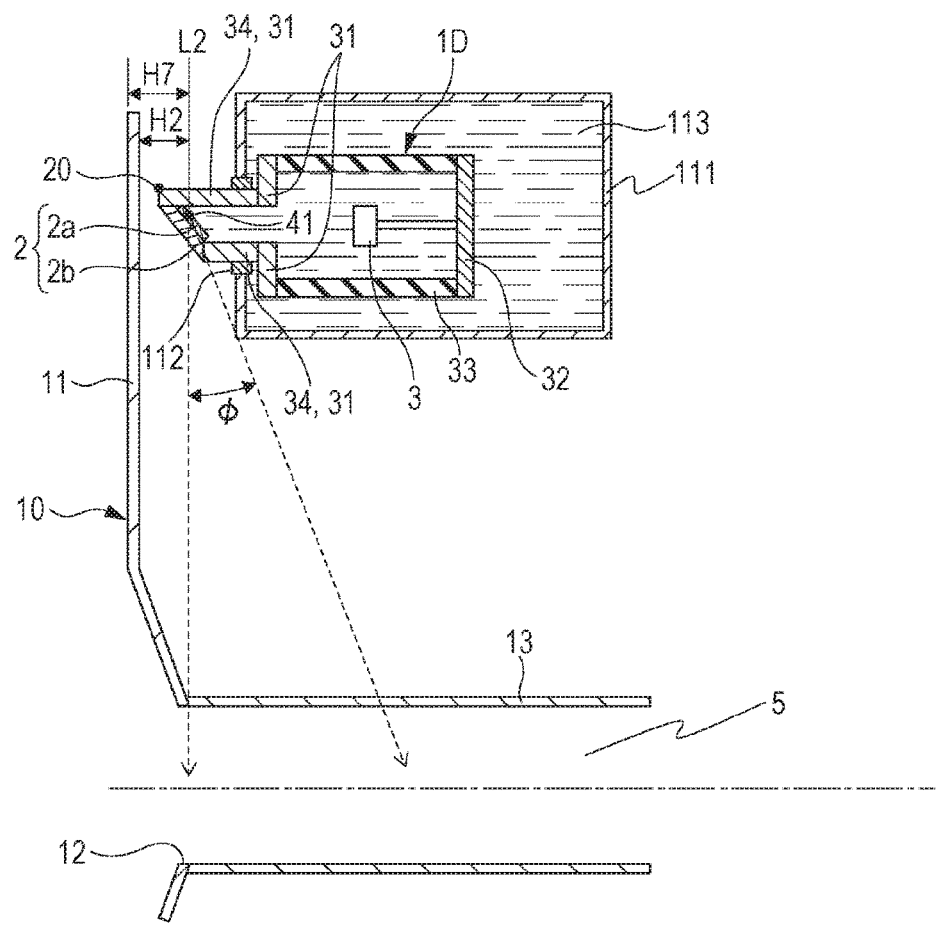

[Fig. 10]
Prior Art
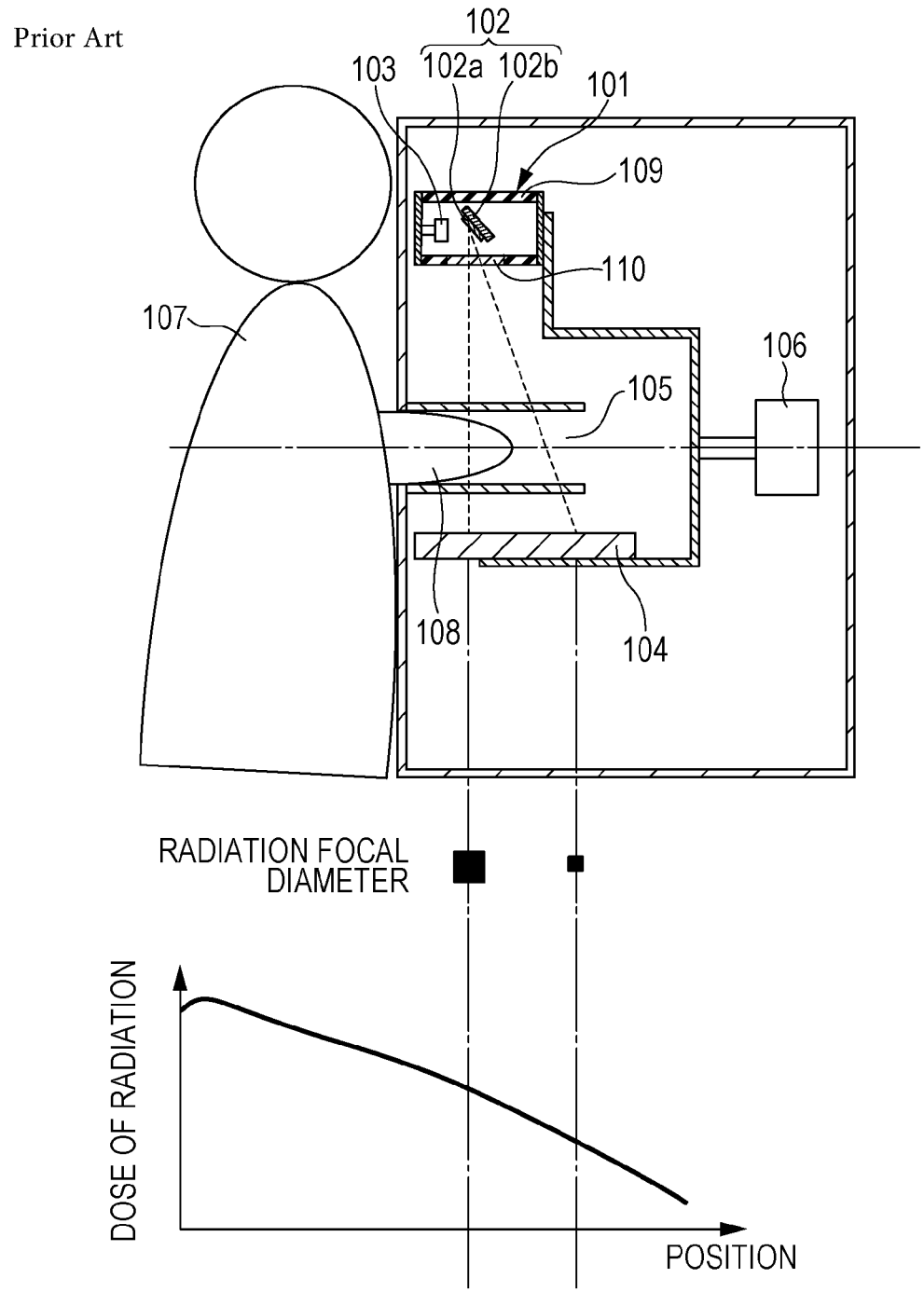

COMPUTED TOMOGRAPHIC MAMMOGRAPHY SYSTEM

TECHNICAL FIELD

The present invention relates to a tomography system in which computed tomography (CT) is executed and more particularly, relates to a computed tomographic mammography system used for imaging a breast.

BACKGROUND ART

Recently, a mammography system which takes a radiographic image of a breast using X-ray, such as the X-ray, has been used for the examination of breast cancer. However, since the image obtained in the mammography system is a plane image, discrimination is sometimes difficult in a case in which a tumor or a calcified portion overlaps, for example, a mammary gland tissue.

For this reason, a computed tomographic mammography system capable of obtaining a three-dimensional (3D) tomographic image by reconstructing a plurality of pieces of image data using computed tomography (CT) has been developed.

A computed tomographic mammography system disclosed in PTL 1 has been proposed. This computed tomographic mammography system includes: a bed for image taking provided with an opening through which a testee puts the breast in a breast chamber; an X-ray tube and an X-ray detecting device which are rotated about the breast chamber; and a rotation driving unit which drives the X-ray tube and the X-ray detecting device to rotate. The X-ray tube and the X-ray detecting device take an X-ray radiographic image at predetermined angles while cooperatively rotating about a rotation axis which passes inside the breast chamber in a direction in which the testee puts the breast in the breast chamber through the opening. Lines 19 and 20 of the 11th column of the specification of PTL 1 describe a computed tomographic mammography system which uses an X-ray source in which a reflective X-ray tube "varian Rad 71" having a rotating anode type anode is housed in a container "Mamrad 100." This X-ray source is disposed to be rotatable about a rotation axis which overlaps a breast chamber.

Further, lines 17 to 19 of the 11th column of the specification of PTL 1 describe providing a distance of 7 cm as a distance between an end of the X-ray source on the testee side and a focal point, and providing a 25-mm-deep bowl-shaped recess in the bed for image taking in order to bring the chest close to an exposure area.

CITATION LIST

Patent Literature

PTL 1: U.S. Pat. No. 6,987,831

SUMMARY OF INVENTION

Technical Problem

FIG. 10 describes a computed tomographic mammography system in which a reflective X-ray tube is used.

In FIG. 10, the reference numeral 101 denotes an X-ray tube which includes a target 102 and an electron emission source 103. The target 102 is a reflective target which includes, on a supporting substrate 102b, a target layer 102a configured to generate X-ray upon irradiation of an electron beam. The X-ray tube 101 faces an X-ray detector 104 via a breast chamber 105. The X-ray tube 101 and the X-ray detector 104 are cooperatively driven by a rotation driving unit 106 to rotate about a rotation axis which passes through the breast chamber 105. X-ray generated upon irradiation of the electron beam from the electron emission source 103 to the target layer 102a passes through a breast 108 of a testee 107, and a necessary X-ray irradiation area on the X-ray detector 104 is irradiated with the X-ray.

Usually, the X-ray tube 101 is disposed with the electron emission source 103 side facing the testee 107 as illustrated. With such an arrangement, an X-ray focal point is seen more obliquely from a nipple side than from a breast wall side, whereby an apparent X-ray focal diameter on the nipple side may be made small as compared with the breast wall side and the resolution may be improved. Usually a mammary gland density is high on the nipple side and discrimination of tiny calcification is difficult, but it is possible to make tiny calcification more findable in an earlier stage by reducing the focal diameter and improving the resolution. Further, by increasing the dose on the breast wall side on which an X-ray transmission distance becomes long, it is possible to prevent a decrease in the dose which passes through the breast wall side.

In the computed tomographic mammography system, in order to reduce overlooking of a lesion or calcification as much as possible, it is desirable to bring the position of the focal point (i.e., an electron beam irradiation region on the target layer 102a) of the X-ray tube 101 to be used close to the breast wall of the testee 107 as much as possible.

However, in a case in which the X-ray tube 101 is a reflection type X-ray tube, the target 102 is contained in a vacuum container 109, and it is necessary to extract X-ray that is generated in the target 102 on the target layer 102a side (i.e., on the back side) to the outside from a window 110 formed in the vacuum container 109. A space in which the electron emission source 103 is to be disposed exists behind the target 102. Therefore, since it is necessary to provide a space for containing the containing electron emission source 103 and a distance of a wall portion of the vacuum container 109 which covers the outside of the space between the target 102 and the testee 107, an arrangement structure in which a focal point of X-ray is brought close to the testee 107 is difficult to be achieved. For this reason, there is a problem that a blind area that is not irradiated with X-ray and thus is not able to be imaged is likely to be produced near the breast wall of the testee 107.

Although the above problem can be solved by reversing the positional relationship between the target 102 and the electron emission source 103 from the relationship illustrated in FIG. 10, there arises a problem that changes in the focal diameter and in the dose of X-ray are reversed from those described above, whereby desirable imaging conditions am not easily obtained.

As described in, for example, PTL 1, there is another method for bringing the bringing focal position close to the breast wall by forming a portion around an opening of a bed for image taking in a recessed shape and disposing an X-ray tube outside the recessed portion.

However, the configuration in which a portion around an opening of a bed for image taking is formed as a recessed portion and an X-ray tube is disposed outside the recessed portion forces the testee to take a posture with the back curved outward. For that reason, in a case in which the distance between the focal point and an outer surface of the vacuum container of the X-ray tube is long, the depth of the recessed portion becomes long, whereby the testee is requested to take a posture with the back curved outward greatly and which is painful. Therefore, usability is decreased.

Solution to Problem

The present invention has been made in view of the above mentioned problems involved with the related art and an object thereof is to reduce a blind area while maintaining desirable imaging conditions in a computed tomographic mammography system.

To achieve the above object, the present invention provides a computed tomographic mammography system, including: an X-ray tube and an X-ray detector disposed to face each other on both sides of a breast chamber; a rotation driving unit which drives the X-ray tube and the X-ray detector cooperatively about a rotation axis which passes through inside the breast chamber in a direction in which the breast is put in the breast chamber, and a gantry which houses the X-ray tube and the X-ray detector wherein the X-ray tube is a transmission type X-ray tube provided with a transmission type target and an electron emission source which emits an electron beam toward the target.

Advantageous Effects of Invention

A transmission type X-ray tube is used in the computed tomographic mammography system of the present invention. In the transmission type X-ray tube, a target constitutes a part of a vacuum container which is an outer peripheral wall of the X-ray tube. Therefore, a distance between the position of the target and an outer surface of the vacuum container which is an outer peripheral wall of the X-ray tube may be made shorter than in a related art reflective X-ray tube. Accordingly, in the computed tomographic mammography system of the present invention, the target may be brought more close to the breast wall of the testee, and the blind area may be reduced.

Further features of the present invention will become apparent from the following description of exemplary embodiments with reference to the attached drawings.

BRIEF DESCRIPTION OF DRAWINGS

FIG. 1 is a schematic diagram illustrating a first embodiment of a computed tomographic mammography system according to the present invention.

FIG. 2 is a system configuration diagram of a computed tomographic mammography system according to the present invention.

FIG. 3 is an enlarged schematic diagram of an X-ray tube.

FIG. 4 is a schematic diagram illustrating a positional relationship between an X-ray tube and a gantry in the first embodiment of the computed tomographic mammography system according to the present invention.

FIG. 5 is a schematic diagram illustrating a positional relationship between an X-ray tube and a gantry in the first embodiment of the computed tomographic mammography system according to the present invention in a case in which another X-ray tube is used.

FIG. 6 is a schematic diagram illustrating a second embodiment of a computed tomographic mammography system according to the present invention.

FIG. 7 is a schematic diagram illustrating a positional relationship between an X-ray tube and a gantry in a second embodiment of a computed tomographic mammography system according to the present invention.

FIG. 8 is a schematic diagram illustrating a positional relationship between an X-ray tube and a gantry in the second embodiment of the computed tomographic mammography system according to the present invention in a case in which another X-ray tube is used.

FIG. 9A is a schematic diagram illustrating a third embodiment of a computed tomographic mammography system according to the present invention.

FIG. 9B is a schematic diagram illustrating a fourth embodiment of a computed tomographic mammography system according to the present invention.

FIG. 10 is a schematic diagram illustrating a related art computed tomographic mammography system.

DESCRIPTION OF EMBODIMENTS

Hereinafter, embodiments of the present invention will be described with reference to the drawings. In the drawings which will be referred to hereinafter, the same reference numerals denote the same components.

First Embodiment

First, in accordance with FIGS. 1 to 5, a first embodiment of the present invention and a modification will be described.

A computed tomographic mammography system according to the first embodiment includes an X-ray tube 1A and an X-ray detector 4 inside a gantry 10. The X-ray tube 1A is a transmission type X-ray tube. An opening 12 is formed in a front part 11 (i.e., a wall surface on the testee 7 side) of the gantry 10 through which a testee puts the breast in a breast chamber 5. The breast chamber 5 is disposed at a bore 13 surrounded by the gantry 10. The X-ray tube 1A and the X-ray detector 4 are disposed to face each other via the breast chamber 5 and are supported by a support base 14. The support base 14 may be rotated by a rotation driving unit 6. The rotation driving unit 6 drives the support base 14 to rotate, whereby the X-ray tube 1 and the X-ray detector 4 are rotated about a rotation axis 15. The rotation axis 15 is a straight line which passes through the breast chamber 5 in a direction in which a breast 8 is put in the breast chamber 5. An unillustrated collimator for controlling an irradiation area of X-ray may be provided between the X-ray tube 1 and the breast chamber 5.

Next, a system configuration of the computed tomographic mammography system will be described with reference to FIGS. 1 and 2.

A system control unit 21 controls operation of the rotation driving unit 6 which rotates the X-ray tube 1A and the X-ray detector 4, and imaging of the X-ray transmission image using the X-ray tube 1A and the X-ray detector 4.

An X-ray tube driving unit 22 controls occurrence of X-ray from the X-ray tube 1A under the control of the system control unit 21. The X-ray emitted from the X-ray tube 1A is illuminated on the breast 8 put in the breast chamber 5. The X-ray passed through the breast 8 is detected by the X-ray detector 4 and an X-ray transmission image is formed.

The rotation driving unit 6 drives the X-ray tube 1A and the X-ray detector 4 under the control of the system control unit 21. The X-ray tube 1A and the X-ray detector 4 forms an X-ray transmission image at a predetermined timing in accordance with a control signal from the system control unit 21 while cooperatively rotating about the rotation axis 15. In this manner, a plurality of X-ray transmission images of the breast 8 which is a sample taken from different angles are obtained.

The obtained data of the plurality of X-ray transmission images is transmitted to a signal processing unit 23. The signal processing unit 23 performs reconstruction calculation to the data of the plurality of X-ray transmission images, processes a tomographic image signal, and outputs the processed tomographic image signal to the system control unit 21. The system control unit 21 outputs a display signal to a display unit 24 in accordance with the obtained tomographic image signal. The display unit 24 displays an image in accordance with the display signal on a screen as a tomography image of the breast 8.

Next, a configuration of the X-ray tube 1A used in the computed tomographic mammography system of the first embodiment will be described with reference to FIG. 3. The X-ray tube 1A includes an electron emission source 3 which emits electrons and a transmission type target 2 which generates X-ray upon irradiation of electrons. The target 2 consists of a target layer 2a and a supporting substrate 2b. The electron emission source 3 is disposed so that the electron beam is incident vertically on the target layer 2a of the target 2. The target 2 is tilted with respect to the rotation axis 15 so that a surface of the supporting substrate 2b opposite to the side that supports the target layer 2a faces the breast chamber 5.

An anode member 31 is disposed around the target 2 and is electrically connected to the target layer 2a. The supporting substrate 2b is mechanically connected to the anode member 31 and constitutes a part of a vacuum container 9 which is an outer case of the X-ray tube 1A. The electron emission source 3 is electrically connected to a cathode member 32. An insulating tube 33 is held between and is connected mechanically to the anode member 31 and the cathode member 32.

The electron emission source 3 includes an electron emitting portion and, when a high voltage is applied to between the electron emitting portion and the target 2, electrons are emitted from the electron emitting portion, and enter the target layer 2a, thereby generating X-ray. A portion of the target layer 2a at which the X-ray is generated (i.e., an area to be irradiated with an electron beam) is referred to as a focal point. The X-ray generated at the target layer 2a passes through the supporting substrate 2b and is then emitted outside the X-ray tube 1A.

The electron emitting portion of the electron emission source 3 may be made of, for example, a tungsten filament, a hot cathode, such as an impregnated cathode, and a cold cathode, such as a carbon nanotube. An extraction electrode and a convergence electrode (not illustrated) may be provided near the electron emitting portion. In a case in which these electrodes are provided, an electric field formed by the extraction electrode causes the electron emitting portion to emit electrons. The emitted electrons are converged at the convergence electrode and enters the target layer 2a, thereby generating X-ray.

The target layer 2a is disposed on a surface of the supporting substrate 2b on the electron emission source 3 side. The target layer 2a may be desirably made of a material that has high melting point and high X-ray generation efficiency. For example, tungsten, tantalum, molybdenum and alloys thereof may be used. A suitable thickness of the target 2a is 1 to 20 micrometer.

The supporting substrate 2b is desirably made of a material that has enough strength to support the target layer 2a, is not likely to absorb the X-ray generated at the target layer 2a, and has high thermal conductivity so as to quickly radiate the heat generated at the target layer 2a. For example, diamond, silicon carbide and aluminum nitride may be used.

Next, a positional relationship among the electron emission source 3 and the target 2 of the X-ray tube 1A, and the front part 11 of the gantry 10 in this example will be described with reference to FIG. 4. The front part of the gantry 10 corresponds to a wall surface of the gantry 10 on the testee 7 side.

In FIG. 4, a virtual plane which passes through a focal center 41 and is in parallel with the front part 11 of the gantry 10 is defined as L1. A tube axial direction of the X-ray tube 1A is tilted with respect to the front part 11. The X-ray tube 1A has a proximal point 20 nearest to the front part 11 in the anode member 31. H1 is a distance between the focal center 41 and the proximal point 20. H2 is a distance between an inner wall of the front part 11 of the gantry 10 and the focal center 41. The inner wall of the front part 11 is a surface which faces the X-ray tube 1A. H3 is a distance between the inner wall of the front part 1 of the gantry 10 and the proximal point 20. H3 is the longer one of the following two distances: a distance of a space necessary for the X-ray tube 1A so as not to be in contact with the front part 11 while rotating; and a distance of a space necessary for secure pressure resistance between the X-ray tube 1A and the front part 11. H4 is a thickness of the front part 11 of the gantry 10. H5 is a distance represented by the sum of H2 and H4, and is a distance between the focal point and a breast wall of the testee 7 (see FIG. 1). If H5 is long, a taken image near the breast wall is missing. Therefore, it is desirable to make H5 small as much as possible. H6 is a distance between the inner wall of the front part 11 of the gantry 10 and the electron emitting portion of the electron emission source 3. In this example, as illustrated in FIG. 4, it is desirable that the target 2 and the electron emission source 3 are disposed in the gantry 10 so that a distance H2 between the inner wall of the front part 11 of the gantry 10 and the focal center 41 is shorter than the distance H6 between the inner wall of the front part 11 of the gantry 10 and the electron emitting portion of the electron emission source 3. By disposing in this manner, the proximal point 20 may be positioned near the target 2 and the focal center 41 may be positioned close to the front part 11. In the present embodiment, the target 2 is rotated on a virtual plane which is perpendicular to the rotation axis 15. The virtual plane which is perpendicular to the rotation axis 15 includes a virtual plane L1 of FIG. 4. Further, the electron emission source 3 is located farther from the testee than the virtual plane L1. By disposing in this manner, it is possible to position the target 2 near the front part 11 without being restricted by the arrangement of the electron emission source 3 and, as illustrated in FIG. 1, it is possible to position the focal center 41 near the front part 11. It is considered also that the virtual plane L1 is defined by a locus of the target 2 that is rotated about the rotation axis 15. In the present embodiment, it is considered also that the tube axial direction of the X-ray tube 1A is defined to be a direction toward the electron emission source 3 from the target 2, a length of the tube axial direction of the X-ray tube 1A is longer than the length of a tube radial direction which is perpendicular to the tube axial direction, and the tube axial direction is tilted away from the testee.

When an acceleration voltage applied to between the target 2 and the electron emitting portion of the electron emission source 3 is set to Va(V), it is desirable to set a potential of the target 2 to a ground potential (0 V) and set a potential of the electron emitting portion of the electron emission source 3 to −Va(V). Since the gantry 10 which includes the front part 11 is an interface that is in contact with the testee, the potential of the gantry 10 is usually defined to be a ground potential. This is because, by setting the distance H2 to be shorter than the distance H6, the distance H3 may be shortened while securing the pressure resistance between the electron emission source 3 and the front part 11.

It is desirable that the target 2 is tilted with respect to the rotation axis 15 as illustrated in FIG. 4. By disposing the target 2 to be tilted with respect to the rotation axis 15, a distance H1 between the focal center 41 and the proximal point 20 may be further shortened. Thereby, the distance H2 between the inner wall of the front part 11 and the focal center 41 may be further shortened. Regarding a tilt angle theta of the target 2 with respect to the rotation axis 15, the distance H1 may be shortened as the absolute value of theta becomes close to 90 degrees from 0 degrees; however, as theta becomes large, an extraction angle of X-ray toward the testee 7 (see FIG. 1) becomes small. When the extraction angle of X-ray necessary for imaging is denoted by phi, a range of the tilt angle theta is expressed by −90 degrees<theta<(90-phi) degrees. In a case in which the electron emission source 3 and the target 2 are disposed so that the distance H2 between the inner wall of the front part 11 and the focal center 41 is shorter than the distance H6 between the inner wall of the front part 11 and the electron emitting portion, the desirable range of theta is 0 degrees<theta<(90-phi) degrees in accordance with the positional relationship of the electron emission source 3 and the target 2.

As described above, according to this example, the distance H1 between the focal center 41 and the proximal point 20 and the distance H2 between the inner wall of the front part 11 and the focal center 41 may be shortened, whereby a distance H5 between the focal center 41 and the breast wall may be shortened. Specifically, the distance H5 between the focal center 41 and the breast wall may be set to about 5 to 10 mm. With this configuration, a computed tomographic mammography system capable of taking a tomographic image of the breast 8 including an area near the breast wall without forcing the testee 7 (see FIG. 1) to take an unnatural posture may be provided.

Next, a modification in which another X-ray tube 1B is used in the first embodiment described above will be described with reference to FIG. 5. In the modification illustrated in FIG. 5, the direction in which the electron beam from the electron emission source 3 is emitted is defined to be in parallel with the rotation axis 15. In the present embodiment, the target 2 is tilted with respect to the irradiated electron beam so that the electron beam is irradiated to the target layer 2a obliquely. The supporting substrate 2b is tilted with respect to the rotation axis 15 so as to face the breast chamber 5, and is tilted also with respect to the direction in which the electron beam is emitted. The tube axial direction of the X-ray tube 1B is disposed to cross the front part 11. The X-ray tube 1B includes a proximity part 30 which is located nearest to the front part 11 on the side on which the anode member 31 faces the front part 11.

With this configuration, it is possible to secure intensity of X-ray with which the breast is irradiated while the distance H1 between the focal center 41 and the proximal point 20 and the distance H2 between the inner wall of the front part 11 and the focal center 41 may be shortened. Other configurations, positional relationships and angular relationships are the same as those of the first embodiment.

Second Embodiment

Next, a second embodiment of the present invention and a modification thereof will be described with reference to FIGS. 6 to 8.

As illustrated in FIG. 6, a computed tomographic mammography system of this example is characterized in that a portion near an opening 12 of a front part 11 of a gantry 10 is recessed inside the gantry 10: other components are the same as those of the first embodiment.

A positional relationship among an electron emission source 3 and a target 2 of an X-ray tube 1A, and the front part 11 of the gantry 10 of this example will be described with reference to FIG. 7. In FIG. 7, the X-ray tube 1A is disposed so that a focal center 41 is located on an extension line L2 of an end surface of a breast chamber 5 on the opening 12 side. With this configuration, it is possible to take an image of a breast of a testee 7 (see FIG. 1) to a position nearest to the breast wall. H1, H2, H3, H4 and H6 are the same as those of the first embodiment. H7 is a depth of the recessed portion. H7 is expressed by the sum of H2 and H4. A tube axial direction of the X-ray tube 1A is tilted with respect to the front part 11, and the X-ray tube 1A has a proximal point 20 nearest to the front part 11 in the anode member 31 as in the first embodiment.

In this example, the positional relationship among the electron emission source 3, the target 2 and the front part 11 of the gantry 10 may be determined to be the same as that of the first embodiment. As described in the first embodiment, according to the present invention, H1 may be shortened, whereby H2 and H7 may be shortened. H7 in this example corresponds to H5 in the first embodiment. According to the present invention, since H5 may be shorted as described above, H7 may be shortened similarly. Since the portion around the opening 12 is recessed and the testee puts the chest in this recessed portion, it is possible to reduce a blind area to substantially 0 and, at the same time, since a depth of the recessed portion is relatively shallow, it is possible to reduce a situation in which the testee 7 (see FIG. 1) is forced to take an unnatural posture. As described above, according to this example, a computed tomographic mammography system capable of taking a tomographic image of the breast including an area nearer the breast wall without forcing the testee 7 to take an unnatural posture may be provided.

FIG. 8 is the same as that of the second embodiment except that the X-ray tube 1B that is the same as that described with reference to FIG. 5 is used. In this example, as in the description of the modification of the first embodiment, it is easy to define the distance H1 between the focal center 41 and the proximal point 20 and the distance H2 between an inner wall of the front part 11 and the focal center 41 to be shorter. Further, a tube axial direction of the X-ray tube 1B is disposed to cross perpendicularly the front part 11. The X-ray tube 1B includes a proximity part 30 which is located nearest to the front part 11 on the side on which the anode member 31 faces the front part 11 as in the embodiment illustrated in FIG. 5.

Third Embodiment

Next, a third embodiment of the present invention will be described with reference to FIG. 9A. This example is an example in which an X-ray tube 1C in which a target 2 of an X-ray tube is connected to an outer surface, and a front shielding body 91 is provided is used. Other portions are the same as those of the first or second modifications. A tube axial direction of the X-ray tube 1C is disposed to perpendicularly cross a front part 11. Further, the X-ray tube 1C includes a proximity part 30 in which the front shielding body 91 projecting toward the breast chamber 5 from the anode member 32 is located nearest to the front part 11 on the side facing the front part 11.

The front shielding body 91 is located on the target 2 on the side opposite to the side on which the target 2 faces the electron emission source 3 and is connected to the target 2. The front shielding body 91 is located between a focal center 41 and the front part 11 of a gantry 10. The front shielding body 91 regulates an angle at which X-ray is emitted from the target 2 and blocks unnecessary X-ray, thereby reducing unnecessary exposure of the testee 7 (see FIG. 1) to the X-ray. In the X-ray tube 1C of this example, since it is possible to provide the front shielding body 91 and connect the front shielding body 91 with the target 2, unnecessary X-ray may be shielded near a position where the X-ray is emitted. Therefore, unnecessary X-ray may be shielded with a simpler configuration without the need of covering the entire X-ray tube 1C with an X-ray shielding member. Further, in this example, a distance H2 between the focal center 41 and an inner wall of the front part 11 of the gantry 10 may be shortened as compared with a related art even after the front shielding body 91 is provided.

In this example, an unillustrated rear shielding body may be provided in the target 2 on the electron emission source 3 side. The rear shielding body is provided in the target 2 on the electron emission source 3 side to cover a periphery of an incident electron beam. The rear shielding body is for shielding unnecessary X-ray that is generated at the target 2 and is emitted on the electron emission source 3 side. As a material which constitutes the front shielding body 91 and the unillustrated rear shielding body, a metallic material, such as, for example, tungsten, tantalum and copper, may be used.

As described above, according to the third embodiment of the present invention, a computed tomographic mammography system capable of taking a tomographic image of the breast 8 including an area nearer to a breast wall without forcing the testee 7 (see FIG. 1) to take an unnatural posture may be provided.

Fourth Embodiment

Next, a fourth embodiment of the present invention will be described with reference to FIG. 9B. This is an example in which an X-ray tube 1D is used of which an anode member 31 differs in shape from those of the above-described X-ray tubes and in which the X-ray tube 1D is housed in a container 111. Other portions are the same as those of the first or second modifications.

The anode member 31 of the X-ray tube 1D includes a protruding portion 34 protruding in the direction away from an insulating tube 33 in a tube axial direction. The target 2 is held by the anode member 31 at the protruding portion 34 of the anode member 31. The tube axial direction of the X-ray tube 1D is disposed to cross perpendicularly a front part 11. The X-ray tube 1D includes a proximal point 20 at which the protruding portion 34 of the anode member 31 is located nearest to the front part 11 on the side facing the front part 11.

Further, the X-ray tube 1D may be housed in the container 111 as illustrated in FIG. 9B. The container 111 may be a metal vessel made of brass, stainless steel, aluminum or the like. An unillustrated driving circuit for driving the X-ray tube 1D may be provided inside the container 111. A remaining space of the container 111 may be provided with a cooling medium 113. The cooling medium 113 is desirably a medium that has a function as a cooling medium of the X-ray tube 1D and as an insulating medium to a high voltage applied to the X-ray tube 1D. As the cooling medium 113, electric insulating oil, such as mineral oil and silicone oil, and a fluorine-based insulating liquid may be used.

The container 111 includes an opening 112, and the X-ray tube 1D is disposed so that at least a part of the protruding portion 34 protrudes outside the container 111 from the opening 112. The target 2 is held by the protruding portion 34 protruding outside the container 111 and is disposed between the container 111 and the front part 11 of the gantry 10.

In a case in which the cooling medium 113 is provided inside the container 111, the protruding portion 34 and the container 111 are connected mechanically to each other and an airtight container is formed. The protruding portion 34 and the container 111 may be connected by, for example, welding, soldering, connecting using brazing metal, an adhesive or the like, or screwing using an O ring or a metal sealing agent.

Desirably, the protruding portion 34 and the container 111 are connected thermally. This is because, by radiating the heat generated in the target 2 in the container 111 through the protruding portion 34, a temperature rise in the target 2 may be suppressed.

According to the X-ray tube 1D of this example, since the protruding portion 34 is provided in the anode member 31 and the target 2 is disposed in the protruding portion 34, the distance H2 between the focal center 41 and the inner wall of the front part 11 of the gantry 10 may be shortened to the same extent as that of the first or the second modification.

In a case in which the X-ray tube 1D is housed in the container 111, since the protruding portion 34 in which the target 2 is disposed is protruded outside the container 111, the focal center 41 may be brought close to the front part 11 of the gantry 10 while securing a radiating angle phi of X-ray. Therefore, also in a case in which the X-ray tube 1D is housed in the container 111, the distance H2 between the focal center 41 and the inner wall of the front part 11 of the gantry 10 may be shortened to the same extent as that of the first or the second modification.

Therefore, according to this example, a computed tomographic mammography system capable of taking a tomographic image of the breast 8 including an area near a breast wall without forcing the testee 7 (see FIG. 1) to take an unnatural posture may be provided.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application No. 2013-193906, filed Sep. 19, 2013, which is hereby incorporated by reference herein in its entirety.

The invention claimed is:

1. A computed tomographic mammography system, comprising:
a transmission type X-ray tube including a transmission type target and an X-ray detector disposed to face each other via a breast chamber;
a rotation unit which rotates the X-ray tube and the X-ray detector cooperatively around a rotation axis which is in the breast chamber; and a gantry which houses the X-ray tube and the X-ray detector and has a front part with an insertion opening for a breast, wherein the transmission type X-ray tube includes an electron emission source configured to emit an electron beam toward the transmission type target, wherein the transmission type target includes a target layer which generates X-ray upon irradiation of electrons, and a supporting substrate which supports the target layer, wherein the supporting substrate is configured to face toward a front part side of the gantry.

2. The computed tomographic mammography system according to claim 1, wherein the target is rotated on a virtual plane which is perpendicular to the rotation axis, and the electron emission source is located farther from a testee than the virtual plane.

3. The computed tomographic mammography system according to claim 1, wherein the electron emission source is located farther from a testee than a virtual plane defined by a locus of the target that is rotated.

4. The computed tomographic mammography system according to claim 1, wherein a tube axial direction of the X-ray tube is defined to be a direction toward the electron emission source from the target, a length of the tube axial direction of the X-ray tube is longer than a length of a tube radial direction which is perpendicular to the tube axial direction, and the tube axial direction is tilted away from a testee.

5. The computed tomographic mammography system according to claim 1, wherein the target is tilted with respect to the electron beam so that the electron beam is irradiated to the target layer obliquely.

6. The computed tomographic mammography system according to claim 1, wherein the target and the electron emission source are disposed so that a distance between the front part which is a wall surface of the gantry on a testee side and a focal center of the X-ray tube is shorter than a distance between the front part of the gantry and an electron emitting portion of the electron emission source.

7. The computed tomographic mammography system according to claim 6, wherein, when an acceleration voltage applied to between the electron emitting portion and the target is set to Va(V), a potential of the target is a ground potential (0 V) and a potential of the electron emitting portion is −Va(V).

8. The computed tomographic mammography system according to claim 6, wherein a portion around the insertion opening is recessed inside the gantry.

9. The computed tomographic mammography system according to claim 6, wherein the X-ray tube includes an anode and a cathode which face each other with an insulating tube held therebetween, the anode including the target and an anode member that holds the target, and the anode member including a portion protruding in a direction away from the insulating tube in a tube axial direction, and the target is held by the anode member at the portion of the anode member and is located between the front part and the insulating tube.

10. The computed tomographic mammography system according to claim 9, wherein the X-ray tube is housed, together with a cooling medium, in a container which includes metal, the container includes an opening, the anode member protrudes in the tube axial direction from the opening of the container, and the target is located between the container and the front part.

11. The computed tomographic mammography system according to claim 1, wherein, when an extraction angle of X-ray is denoted by phi, a tilt angle theta of the target with respect to the rotation axis is expressed by −0 degrees<theta<(90-phi) degrees.

12. The computed tomographic mammography system according to claim 1, wherein the X-ray tube includes a front shielding body which is connected to the target on the supporting substrate side and which regulates an angle at which X-ray is emitted from the target.

13. A computed tomographic mammography system, comprising:

an X-ray tube and an X-ray detector disposed to face each other on both sides of a breast chamber;

a rotation unit which rotates the X-ray tube and the X-ray detector around a rotation axis which is in the breast chamber; and a gantry which houses the X-ray tube and the X-ray detector, wherein the X-ray tube is a transmission type X-ray tube provided with a transmission type target and an electron emission source which emits an electron beam toward the target, wherein the target is rotated on a virtual plane which is perpendicular to the rotation axis, and the electron emission source is located farther from a testee than the virtual plane.

14. The computed tomographic mammography system according to claim 13, wherein the electron emission source is located farther from the testee than the virtual plane defined by a locus of the target that is rotated.

15. The computed tomographic mammography system according to claim 13, wherein a tube axial direction of the X-ray tube is defined to be a direction toward the electron emission source from the target, a length of the tube axial direction of the X-ray tube is longer than a length of a tube radial direction which is perpendicular to the tube axial direction, and the tube axial direction is tilted away from the testee.

16. The computed tomographic mammography system according to claim 13, wherein the target is tilted with respect to the electron beam so that the electron beam is irradiated to the target layer obliquely.

17. The computed tomographic mammography system according to claim 13, wherein the target and the electron emission source are disposed so that a distance between a front part which is a wall surface of the gantry on a testee side and a focal center of the X-ray tube is shorter than a distance between the front part of the gantry and an electron emitting portion of the electron emission source.

18. The computed tomographic mammography system according to claim 17, wherein, when an acceleration voltage applied to between the electron emitting portion and the target is set to Va(V), a potential of the target is a ground potential (0 V) and a potential of the electron emitting portion is −Va(V).

19. The computed tomographic mammography system according to claim 17, wherein an opening from which a breast is put in the breast chamber is provided in the front part of the gantry and a portion around the opening is recessed inside the gantry.

20. The computed tomographic mammography system according to claim 17, wherein the X-ray tube includes an anode and a cathode which face each other with an insulating tube held therebetween, the anode including the target and an anode member that holds the target, and the anode member including a portion protruding in a direction away from the insulating tube in a tube axial direction, and the target is held by the anode member at the portion of the anode member and is located between the front part and the insulating tube.

21. The computed tomographic mammography system according to claim 20, wherein the X-ray tube is housed, together with a cooling medium, in a container which includes metal, the container includes an opening, the anode member protrudes in the tube axial direction from the opening of the container, and the target is located between the container and the front part.

22. The computed tomographic mammography system according to claim 13, wherein, when an extraction angle of X-ray is denoted by phi, a tilt angle theta of the target with respect to the rotation axis is expressed by −0 degrees<theta<(90-phi) degrees.

23. The computed tomographic mammography system according to claim 13, wherein the X-ray tube includes a front shielding body which is connected to the target on a supporting substrate side and which regulates an angle at which X-ray is emitted from the target.

24. A computed tomographic mammography system, comprising:
    an X-ray tube and an X-ray detector disposed to face each other on both sides of a breast chamber;
    a rotation unit which rotates the X-ray tube and the X-ray detector around a rotation axis which is in the breast chamber; and
    a gantry which houses the X-ray tube and the X-ray detector,
    wherein the X-ray tube is a transmission type X-ray tube provided with a transmission type target and an electron emission source which emits an electron beam toward the target,
    wherein, when an extraction angle of X-ray is denoted by phi, a tilt angle theta of the target with respect to the rotation axis is expressed by −0 degrees<theta<(90-phi) degrees.

25. The computed tomographic mammography system according to claim 24, wherein the electron emission source is located farther from a testee than a virtual plane defined by a locus of the target that is rotated.

26. The computed tomographic mammography system according to claim 24, wherein a tube axial direction of the X-ray tube is defined to be a direction toward the electron emission source from the target, a length of the tube axial direction of the X-ray tube is longer than a length of a tube radial direction which is perpendicular to the tube axial direction, and the tube axial direction is tilted away from a testee.

27. The computed tomographic mammography system according to claim 24, wherein the target is tilted with respect to the electron beam so that the electron beam is irradiated to the target layer obliquely.

28. The computed tomographic mammography system according to claim 24, wherein the target and the electron emission source are disposed so that a distance between a front part which is a wall surface of the gantry on a testee side and a focal center of the X-ray tube is shorter than a distance between the front part of the gantry and an electron emitting portion of the electron emission source.

29. The computed tomographic mammography system according to claim 28, wherein, when an acceleration voltage applied to between the electron emitting portion and the target is set to Va(V), a potential of the target is a ground potential (0 V) and a potential of the electron emitting portion is −Va(V).

30. The computed tomographic mammography system according to claim 28, wherein an opening from which a breast is put in the breast chamber is provided in the front part of the gantry and a portion around the opening is recessed inside the gantry.

31. The computed tomographic mammography system according to claim 28, wherein the X-ray tube includes an anode and a cathode which face each other with an insulating tube held therebetween, the anode including the target and an anode member that holds the target, and the anode member including a portion protruding in a direction away from the insulating tube in a tube axial direction, and the target is held by the anode member at the portion of the anode member and is located between the front part and the insulating tube.

32. The computed tomographic mammography system according to claim 31, wherein the X-ray tube is housed, together with a cooling medium, in a container which includes metal, the container includes an opening, the anode member protrudes in the tube axial direction from the opening of the container, and the target is located between the container and the front part.

33. The computed tomographic mammography system according to claim 24, wherein the X-ray tube includes a front shielding body which is connected to the target on a supporting substrate side and which regulates an angle at which X-ray is emitted from the target.

* * * * *